United States Patent
de la Poterie

(10) Patent No.: US 6,238,679 B1
(45) Date of Patent: May 29, 2001

(54) FILM-FORMING COMPOSITION COMPRISING A POLYURETHANE IN AQUEOUS DISPERSION AND A PLASTICIZER

(75) Inventor: Valérie de la Poterie, Le Chatelet en Brie (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/264,857

(22) Filed: Mar. 9, 1999

(30) Foreign Application Priority Data

Mar. 9, 1998 (FR) .................................................. 98 02838

(51) Int. Cl.$^7$ .............................. A61K 6/00; A61K 7/00; A61K 7/04; A61K 7/025
(52) U.S. Cl. ................................ 424/401; 424/61; 424/64
(58) Field of Search ............................. 424/401, 61, 64, 424/70.7, 485, 488

(56) References Cited

U.S. PATENT DOCUMENTS

| 5,538,717 | 7/1996 | La Poterie | 424/61 |
| 5,601,808 | * 2/1997 | Mellul et al. | 424/61 |
| 5,683,681 | * 11/1997 | Ramin et al. | 424/61 |
| 5,807,540 | 9/1998 | Junino et al. | 424/61 |
| 5,830,443 | 11/1998 | Lee | 424/61 |
| 5,972,354 | * 10/1999 | De La Poterie et al. | 424/401 |

FOREIGN PATENT DOCUMENTS

| 0 143 480 | 6/1985 | (EP) . |
| 0 613 676 | 9/1994 | (EP) . |
| 0 637 600 | 2/1995 | (EP) . |
| 0 648 485 | 4/1995 | (EP) . |
| 0 658 609 | 6/1995 | (EP) . |
| 0 679 384 | 11/1995 | (EP) . |
| 0 740 933 | 11/1996 | (EP) . |
| 0 775 483 | 5/1997 | (EP) . |
| 3-112916 | 5/1991 | (JP) . |
| 11-92653 | 4/1999 | (JP) . |
| WO 96/14050 | 5/1996 | (WO) . |
| WO 96/14059 | 5/1996 | (WO) . |

OTHER PUBLICATIONS

Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104–117.
English language Derwent Abstract of EP 0 637 600.
English language Derwent Abstract of EP 0 648 485.
English language Derwent Abstract of EP 0 658 609.
English language Derwent Abstract of EP 0 775 483.
English language Derwent Abstract of JP 31–112916.
Patent Abstracts of Japan, JP 11–92653, Apr. 6, 1999.

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

The invention relates to a film-forming composition comprising at least one aqueous dispersion of poly urethane particles and at least one plasticizer chosen from solvents having an average Hansen solubility parameter dH at 25° C. such that $dH \leq 8$ $(J/cm^3)^{1/2}$, and to its use in a process for making up keratin substances and/or mucous membranes. The invention also relates to the use of the aqueous dispersion of polyurethane particles and of the plasticizer to obtain a film-forming composition whose viscosity is stable over time and/or which does not solidify over time.

22 Claims, No Drawings

FILM-FORMING COMPOSITION COMPRISING A POLYURETHANE IN AQUEOUS DISPERSION AND A PLASTICIZER

The invention relates to a film-forming composition, in particular a topical composition, comprising a film-forming polyurethane intended in particular for the cosmetic and/or dermatological fields. The invention also relates to a use of this composition to treat and care for keratin substances such as the skin, the nails, the eyelashes, the eyebrows, the hair or mucous membranes such as the lips and the inside of the eyelids. The invention is intended more especially to treat and/or care for the nails.

Make-up compositions for the nails and the lips, comprising a polyurethane in aqueous dispersion as film-forming polymer, are known from patent applications EP-A-143,480, EP-A-648,485 and EP-A-775,483.

The film deposited on the nail or the lips after a film-forming composition has been applied should have good flexibility to prevent it from cracking or flaking. With this aim, it is a common practice to add plasticizers to the film-forming composition, allowing the flexibility of the film to be adjusted without weakening its physical strength.

Document EP-A-775,483 describes a lipstick composition comprising an aqueous polyurethane dispersion plasticized with glycerol. Glycerol has a Hansen solubility parameter dH at 25° C. equal to 29.30.

Document EP-A-637,600 describes nail varnish compositions comprising an aqueous polyester-polyurethane dispersion and a plasticizing solvent such as dipropylene glycol n-butyl ether, which has a Hansen solubility parameter dH at 25° C. equal to 8.7, or propylene glycol monophenyl ether, which has a Hansen parameter dH at 25° C. equal to 13.

Varnishes in an organic solvent medium containing a citrate are also known from documents EP-A-613,676 and JP-A03,112,916.

Moreover, film-forming compositions such as nail varnishes should have certain rheological properties, such as low viscosity, in order to make them easy to apply, in particular using a brush. With this aim, it is desirable for the composition not to become thick in the bottle over time and thus to remain stable throughout the period of storage.

However, the inventor has found that compositions comprising an aqueous polyurethane dispersion and certain plasticizers have a tendency to thicken over time. This increase in viscosity takes place more particularly when the composition is stored at high temperature, in particular at and above 45° C., and especially after one week, or alternatively several months at room temperature. The composition thus thickened is difficult to apply and does not give a deposit of a uniform and continuous film. Certain plasticizers even solidify inside the bottle, making the composition unusable.

The aim of the invention is to propose a film-forming composition containing an aqueous dispersion of polyurethane particles which has good cosmetic and/or stability properties and does not have the disadvantages mentioned above.

The inventor has discovered that such a composition can be obtained by using a specific selection of plasticizers. These plasticizers allow the composition to be stored at high temperature, in particular at 45° C., for two weeks or even several months, while avoiding any substantial increase in the Viscosity of the composition over time. A film-forming composition whose viscosity is stable over time is thus obtained. The composition is easy to apply, in particular using a brush, onto the support to be treated, such as, for example, keratin substances.

The subject of the invention is a film-forming composition comprising at least one aqueous dispersion of polyurethane particles and at least one plasticizer, characterized in that the plasticizer is chosen from solvents with an average Hansen solubility parameter dH at 25° C. such that $dH \leq 8$ $(J/cm^3)^{1/2}$.

Preferably, the plasticizer according to the invention can also have an average Hansen solubility parameter dP at 25° C. such that $dP \leq 3$ $(J/cm^3)^{1/2}$, and better still $dP \leq 2$ $(J/cm^3)^{1/2}$.

The definition of the solvents in the three-dimensional solubility space according to Hansen is described in the article by C. M. Hansen: "The three dimensional solubility parameters" J. Paint Technol. 39, 105 (1967), which is specifically incorporated by reference herein;

dH characterizes the specific interaction forces (such as hydrogen bonding, acid/base, donor/acceptor, etc. interactions);

dP characterizes the Debye interaction forces between permanent dipoles and the Keesom interaction forces between induced dipoles and permanent dipoles.

The parameters dP and dH are expressed in $(J/cm^3)^{1/2}$.

According to the invention, the plasticizer can be chosen from C3–C10 dialkyl adipates, C3–C10 dialkyl phthalates and acetyl tributyl citrate.

Preferably, the plasticizer can be chosen from dibutyl phthalate (dH=7.5; dP=2.8), bis(2-ethylhexyl) phthalate (dH=5.92; dP=1.76), diisopropyl adipate (dH=7.76; dP=2.98), dibutyl adipate (dH=7.28; dP 2.63), bis(2-ethylhexyl) adipate (dH=5.97; dP 1.76) and acetyl tributyl citrate (dH=7.09; dP 1.75).

Preferably, the plasticizer can be chosen from dibutyl phthalate, diisopropyl adipate, bis(2-ethylhexyl) adipate and acetyl tributyl citrate.

The polyurethane in aqueous dispersion can preferably be an anionic polyurethane. This anionic nature is due in particular to the presence of groups containing a carboxylic acid or sulphonic acid functional group in the polymer.

According to the invention, one or more aqueous dispersions of one or more polyurethanes can be used.

The polyurethane can preferably be chosen from polyesterpolyurethanes and polyetherpolyurethanes, and preferably from anionic polyesterpolyurethanes.

Advantageously, the aqueous polyurethane dispersion can be chosen from those in which the polyurethane particle size ranges from 2 to 100 nm and in which the hardness of a film obtained after drying, for 24 hours at 30° C. and at 50% relative humidity, of a layer 300 μm thick (before drying) of an aqueous dispersion containing 28% solids of the said polyurethane particles ranges from 15 to 300 seconds.

The hardness of the film is measured according to ASTM standard D43-66, or NF-T standard 30-016 (October 1981), using a Persoz balance.

Preferred polyurethanes which can be used according to the invention are the polyesterpolyurethanes sold under the names "Avalure UR-405®", "Avalure UR-425®", "Sancure 2060®" by the company Sanncor and the polyetherpolyurethanes sold under the names "Sancure 878®", by the company Sanncor and "Neorez R 970®" by the company ICI.

According to the invention, the polyurethane can preferably be present in the composition in an amount ranging from 3 to 50% by weight relative to the total weight of the composition, and more preferably from 10% to 35% by weight.

In the composition according to the invention, the plasticizer can preferably be present in an amount ranging from 0.1% to 20% by weight, relative to the total weight of the composition, and more preferably from 0.5% to 10% by weight.

Preferably, the composition according to the invention can additionally contain adjuvants commonly used in cosmetic compositions, in particular topical cosmetic compositions. Examples of adjuvants which may be used are dyes, pigments, pearlescent agents, lakes, anti-UV agents, preserving agents, thickeners, surfactants, waxes, fragrances and moisturizers. Needless to say, a person skilled in the art will take care to select optional adjuvants, and the amount thereof, such that the advantageous properties of the composition according to the invention are not, or are not substantially, adversely affected by the addition envisaged.

The composition according to the invention can advantageously be used to treat, make up or care for keratin substances or mucous membranes depending on the nature of the active agents used. The make-up composition can be a nail varnish, an eyeliner, a mascara, a foundation, a concealer, an eyeshadow, a blusher, a lipstick (lip gloss) or a make-up composition for the body.

The composition according to the invention can advantageously be in the form of a nail varnish or a nailcare composition.

The invention also relates to a cosmetic treatment process or make-up process for keratin substances, and in particular the nails, or mucous membranes, which comprises applying a composition as described above to the keratin substances or the mucous membranes.

A subject of the invention is also the use of at least one aqueous dispersion of polyurethane particles and of at least one plasticizer chosen from solvents having an average Hansen solubility parameter dH at 25° C. such that dH≦8 $(J/cm^3)^{1/2}$ as defined above, in order to obtain a film-forming composition whose viscosity is stable over time and/or which is easy to apply and/or which does not solidify over time.

The examples below are to further illustrate the present invention without, however, limiting it.

Examples 1 to 8

Comparative 3 compositions (E1 to E3) according to the invention and 5 compositions (E4 to E8) not according to the invention were prepared, these compositions being made up as follows:

| | |
|---|---|
| aqueous polyester polyurethane dispersion (Avalure UR-405 ®) | 35 g A.M. |
| plasticizer | 3.5 g |
| water | qs 100 g | using different plasticizers at a content of 10% by weight relative to the weight of polymer.

These compositions were stored at 45° C. for 2 months. The viscosity of each composition was measured at four different times during the storage:

T0=initial time of mixing
T1=T0+1 week
T2=T0+1 month
T3=T0+2 months

The viscosities were measured using a BROOKFIELD RVTDV 2+ viscometer with rotor RV6 at a spin speed of 100 revolutions/minute, after spinning the rotor for 10 minutes, at 25° C.

The following results were obtained, the viscosities being expressed in mPa.s.

| Plasticizer | T0 | T1 | T2 | T3 |
|---|---|---|---|---|
| dibutyl phthalate (E1) | 864 | 989 | 1040 | 1440 |
| bis (ethylhexyl) adipate (E2) | 659 | 682 | 611 | 605 |
| acetyl tributyl citrate (E3) | 957 | 906 | 752 | 656 |
| triethyl citrate* (E4) | 224 | too thick | set to a solid | sets to a solid |
| TPn Bu* (E5) | 704 | 1280 | 4740 | 32,300 |
| ethyl lactate *(E6) | 122 | sets to a solid | sets to a solid | sets to a solid |
| Arcosolv PTB* (E7) | 330 | 595 | 1550 | 5440 |
| Pn Bu* (E8) | 650 | 7420 | 25,100 | too thick |

*plasticizers not forming part of the invention:

triethyl citrate (dH=13.39; dP=4.3)

TPn BU=tripropylene glycol n-butyl ether (dH=10.8; dP=3.4)

Arcosolv PTB: propylene glycol t-butyl ether (dH=12.52; dP=4.37)

Pn Bu: propylene glycol n-butyl ether (dH=12.6; dP=4.4)

The results obtained show that the plasticizers according to the invention can give a film-forming composition, after storage at 45° C., which has a viscosity of not more than 1380 mPa.s, which is markedly less than the viscosities obtained for the compositions comprising a plasticizer not according to the invention, the latter compositions even resulting in the formation of a stick. Thus, only the compositions according to the invention remain fluid after storage and are capable of being applied to the support to be treated, such as the nails or the lips; their viscosity is stable over time.

Examples 9 to 13

Comparative

In the same way as in Example 1, 4 compositions (E9 to E12) according to the invention and one composition (E13) not according to the invention were prepared with the same film-forming polymer, using different plasticizers at a content of 5% by weight (instead of 10% by weight) relative to the total weight of polymer.

The following viscosity results were obtained, expressed in mPa.s:

| Plasticizer | T0 | T1 | T2 | T3 |
|---|---|---|---|---|
| diisopropyl adipate (E9) | 573 | 531 | 598 | 685 |
| dibutyl phthalate (E10) | 538 | 573 | 566 | 611 |
| bis (ethylhexyl) adipate (E11) | 634 | 560 | 522 | 509 |
| acetyl tributyl citrate (E12) | 819 | 653 | 579 | 614 |

-continued

| Plasticizer | T0 | T1 | T2 | T3 |
|---|---|---|---|---|
| triethyl citrate* (E13) | 208 | 806 | too thick | sets to a solid |

*plasticizers not forming part of the invention:

It was found that the composition comprising triethyl citrate (not according to the invention) results, after storage at 45° C. for 1 month, in the formation of a stick, whereas the compositions according to the invention remain fluid, even after storage at 45° C. for two months.

Examples 14 to 17

Comparative

In the same way as in Example 1, 3 compositions (E14 to E16) according to the invention and one composition (E17) not according to the invention were prepared, these compositions being made up as follows:

| | |
|---|---|
| aqueous polyester polyurethane dispersion (Sancure 2060 ®) | 27 g A.M. |
| plasticizer | 2.7 g |
| water | qs 100 g | the plasticizer content being 10% by weight relative to the weight of polymer.

The viscosities were measured at T0, T1 and T2 defined above.

The following viscosity results were obtained, expressed in mPa.s:

| Plasticizer | T0 | T1 | T2 |
|---|---|---|---|
| bis (ethylhexyl) adipate (E14) | 270 | 290 | 270 |
| acetyl tributyl citrate (E15) | 300 | 300 | 330 |
| diisopropyl adipate (E16) | 340 | 400 | 440 |
| TPn Bu* (E17) | 540 | 820 | 1010 |

*plasticizer not forming part of the invention

The results obtained show that the viscosity of the compositions according to the invention is lower than that of the composition comprising TPn Bu (not according to the invention). In addition, only the compositions according to the invention have a viscosity which is stable over time. These more fluid compositions are thus easier to spread, for example with a brush, than the composition comprising TPn Bu.

Examples 18 to 21

Comparative

In the same way as in Example 1, 3 compositions (E18 to E20) according to the invention and one composition (E21) not according to the invention were prepared, these compositions being made up as follows:

| | |
|---|---|
| aqueous polyester polyurethane dispersion (Sancure 878 ®) | 34 g A.M. |
| plasticizer | 3.4 g |
| water | qs 100 g | the plasticizer content being 10% by weight relative to the weight of polymer.

The following viscosity results were obtained, expressed in mpa.s:

| Plasticizer | T0 | T1 | T2 | T3 |
|---|---|---|---|---|
| bis (ethylhexyl) adipate (E18) | 830 | 580 | 760 | 690 |
| acetyl tributyl citrate (E19) | 760 | 520 | 510 | 350 |
| diisopropyl adipate (E20) | 790 | 470 | 410 | 430 |
| TPn Bu* (E21) | 1400 | 1000 | 1230 | 1410 |

*plasticizer not forming part of the invention

The results obtained show that the viscosity of the compositions according to the invention is lower than that of the composition comprising TPn Bu (not according to the invention).

Example 22

A fluid composition to be applied to the lips was prepared, this composition being made up as follows:

| | |
|---|---|
| aqueous polyester-polyurethane dispersion (Avalure UR-425 ®) | 20 g A.M. |
| acetyl tributyl citrate | 1 g |
| pigments | 4 g |
| thickener | 1 g |
| preserving agents qs | |
| water | qs 100 g |

A fluid composition which has good stability on storage and which applies easily to the lips is obtained.

Example 23

A nail varnish having the following composition was prepared:

| | |
|---|---|
| aqueous polyester-polyurethane dispersion (Avalure UR-405 ®) | 30 g A.M. |
| diisopropyl adipate | 3 g |
| pigments | 4 g |
| thickener | 1 g |
| preserving agents qs | |
| water | qs 100 g |

A fluid varnish whose viscosity is stable on storage and which spreads easily on the nails is obtained.

Example 24

An eyeliner having the following composition was prepared:

| | |
|---|---|
| aqueous polyether-polyurethane dispersion (Sancure 878 ®) | 25 g A.M. |
| bis(2-ethylhexyl) adipate | 1.25 g |
| pigments | 13 g |
| preserving agents qs | |
| water | qs 100 g |

A fluid varnish which has good stability on storage and which applies easily to the edge of the eyelids is obtained.

What is claimed is:

1. A film-forming composition comprising at least one aqueous dispersion of polyurethane particles and at least one plasticizer chosen from solvents having an average Hansen solubility parameter dH at 25° C. such that dH≦8 $(J/cm^3)^{1/2}$.

2. The composition according to claim 1, wherein said at least one plasticizer has an average solubility parameter dP at 25° C. such that dP≦3 $(J/cm3)^{1/2}$.

3. The composition according to claim 1, wherein said at least one plasticizer is chosen from $C_3$–$C_{10}$ dialkyl adipates, $C_3$–$C_{10}$ dialkyl phthalates and acetyl tributyl citrate.

4. The composition according to claim 1, wherein said at least one plasticizer is chosen from dibutyl phthalate, bis(2-ethylhexyl) phthalate, diisopropyl adipate, dibutyl adipate, bis(2-ethylhexyl) adipate and acetyl tributyl citrate.

5. The composition according to claim 1, wherein said plasticizer is chosen from dibutyl phthalate, diisopropyl adipate, bis(2-ethylhexyl) adipate and acetyl tributyl citrate.

6. The composition according to claim 1, wherein said polyurethane particles are anionic polyurethane particles.

7. The composition according to claim 1, wherein said polyurethane particles are chosen from polyesterpolyurethane and polyetherpolyurethane particles.

8. The composition according to claim 7, wherein said polyurethane particles are anionic polyesterpolyurethane particles.

9. The composition according to claim 1, wherein the size of said polyurethane particles ranges from 2 to 100 nm and the hardness of a film obtained after drying, for 24 hours at 30° C. and at 50% relative humidity, of a layer 300 μm thick of an aqueous dispersion containing 28% solids of the said polyurethane particles ranges from 15 to 300 seconds.

10. The composition according to claim 1, wherein said polyurethane particles are present in an amount ranging from 3 to 50% by weight relative to the total weight of the composition.

11. The composition according to claim 10, wherein said polyurethane particles are present in an amount ranging from 10% to 35% by weight relative to the total weight of the composition.

12. The composition according to claim 1, wherein said at least one plasticizer is present in an amount ranging from 0.1% to 20% by weight relative to the total weight of the composition.

13. The composition according to claim 12, wherein said at least one plasticizer is present in an amount ranging from 0.5% to 10% by weight relative to the total weight of the composition.

14. The composition according to claim 1, further comprising at least one adjuvant chosen from dyes, pigments, pearlescent agents, lakes, anti-UV agents, preserving agents, thickeners, surfactants, waxes, fragrances and moisturizers.

15. The composition according to claim 1, wherein said composition further comprises at least one adjuvant chosen from pigments and dyes.

16. The composition according to claim 1, wherein said composition further comprises at least one thickener.

17. The composition according to claim 1, wherein said composition is a cosmetic composition to treat, make up or care for keratin substances or mucous membranes.

18. The cosmetic composition according to claim 17, wherein said cosmetic composition is in the form of a make-up composition.

19. The composition of claim 1, wherein said composition is in the form of a nail varnish, a nailcare composition, an eyeliner, a mascara, a foundation, a concealer, an eyeshadow, a blusher, a lipstick, a lipgloss or a make-up composition for the body.

20. A process to cosmetically treat keratin substances or mucous membranes comprising applying to said keratin substances or mucous membranes an effective amount of a composition according to claim 1.

21. A process for making up keratin substances or mucous membranes comprising applying to said keratin substances or mucous membranes an effective amount of a composition according to claim 1.

22. A process of making a film-forming composition whose viscosity is stable over time, which is easy to apply or which does not solidify over time, comprising including in said film-forming composition an effective amount of at least one aqueous dispersion of polyurethane particles and at least one plasticizer chosen from solvents having an average Hansen solubility parameter dH at 25° C. such that dH≦8 $(J/cm^3)^{1/2}$.

* * * * *